US007858831B2

(12) United States Patent
Meyer et al.

(10) Patent No.: US 7,858,831 B2
(45) Date of Patent: Dec. 28, 2010

(54) GENERAL METHOD FOR INCREASING STEREOSELECTIVITY IN STEREOSELECTIVE REACTIONS

(75) Inventors: Matthew P. Meyer, Merced, CA (US); Hui Zhu, Merced, CA (US)

(73) Assignee: The Regents of the University of California, Oakland, CA (US)

( * ) Notice: Subject to any disclaimer, the term of this patent is extended or adjusted under 35 U.S.C. 154(b) by 138 days.

(21) Appl. No.: 12/340,455

(22) Filed: Dec. 19, 2008

(65) Prior Publication Data

US 2009/0163741 A1 Jun. 25, 2009

Related U.S. Application Data

(60) Provisional application No. 61/016,297, filed on Dec. 21, 2007.

(51) Int. Cl.
*C07C 27/04* (2006.01)
*C07C 27/06* (2006.01)
*B01J 19/10* (2006.01)

(52) U.S. Cl. .................. 568/814; 568/880; 568/881; 204/157.62

(58) Field of Classification Search ................ None
See application file for complete search history.

(56) References Cited

PUBLICATIONS

Toukoniitty et al., Ultrasonics Sonochemistry (2006), 13, p. 68-75.*
U.S. Appl. No. 61/016,297, filed Dec. 21, 2007, Meyer et al.
Asano et al., "Activation and Reaction Volumes in Solution," *Chem. Rev.*, (1978) 78:407-489.
Bian et al., "Reductive coupling of aromatic aldehydes using zinc powder in aqueous sodium hydroxide under ultrasound," *Chinese Journal of Synthetic Chemistry*, (2004) 12(5):429-431.
Brown et al., "Ultrasonics in Organoborane Chemistry, A Novel and Powerful Method for Rapid Hydroboration," *Tetrahedron Lett.*, (1985) 26:2187-2190.
Brown et al., "The boron approach to asymmetric synthesis," *Pure & Appl. Chem.*, (1991) 63(3):307-316.
Canet et al., "Enantiomeric Analysis in a Polypeptide Lyotropic Liquid Crystal by Deuterium NMR," *J. Am. Chem. Soc.*, (1995) 117:6520-6526.
Chen et al., "Study of Chiral Auxiliaries for the Intrmolecular [2+2] Cycloaddition of a Keteniminium Salt to an Olefinic Double Bond. An New Asymmetric Synthesis of Cyclobutanones," *Tetrahedron Letters*, (1990) 31(31):4467-4470.
Cherest et al., "Torsional Strain Involving Partial Bonds. The Stereochemistry of the Lithium Aluminum Hydride Reduction of Some Simple Open-Chain Ketones," *Tetrahedron Lett.*, (1968) 9:2199-2204.
Fan et al., "A Mild and Efficient Asymmetric Hetero-Diels—Alder Reaction of the Brassard Diene with Aldehydes ," *Eur. J. Org. Chem.*, (2005), 3542-3552.
Flannigan et al., "Measurement of Pressure and Density Inside a Single Sonoluminescing Bubble," *Phys. Rev. Lett.*, (2006) 96:204301-1-204301-4.

Flint et al., "The Temperature of Cavitation," *Science*, (1991), 253:1397-1399.
Fujikawa et al., "Effects of the Non-equilibrium Condensation of Vapor on the Pressure Wave Produced by the Collapse of a Bubble in a Liquid," *J. Fluid Mech.*, (1980), 97:481-512.
Hickenboth et al., "Biasing Reaction Pathways with Mechanical Force," *Nature*, (2007), 446:423-427.
Jenner, G., "High Pressure and Selectivity in Organic Reactions," *Tetraheron*, (1997), 53:2669-2695.
Jenner, G. "Comparative Acivation Modes in Organic Synthesis. The Specific Role of High Pressure." *Tetrahedron*, (2002), 58:5185-5202.
Katsuki et al., "The First Practical Method for Asymmetric Epoxidation," *J. Am. Chem. Soc.*, (1980), 102:5974-5976.
Kawashima et al., "Sonochemical and triethylborane-induced tin deuteride reduction for the highly stereoselective synthesis of (2'R)-[2'-2H]-2'-deoxyribonucleosides from 2'-functionalized ribonucleosides," *Tetrahedron Letters*, (1993), 34(8):1317-20.
Li et al., "Aluminum/fluoride salt-mediated reductive coupling of aromatic aldehydes in aqueous media under ultrasound irradiation," *Chinese J. of Organic Chemistry*, (2005), 25(12):1583-1586.
Lindley et al., "Sonochemistry Part 2—Synthetic Applications," *Chem. Soc. Rev.*(1987), 16:275-311.
Liu et al., "Chiral oxazaborolidine-aluminum bromide complexes are unusually powerful and effective catalysts for enantioselective Diels-Alder reactions" (2007) *J. Am. Chem. Soc.* 129:1498-1499.
Luche et al., "Can sonication modify the region- and steroselictivities of organic reactions?" *Advances in Sonochemistry*, (1999), 5:147-174.
Matsuda et al., "Ultrasonic Effects on Electroorganic Processes. Product-selectivity in Electroreduction of Benzaldehydes," *Chemistry Letter*, (1994), (9):1619-22.
Matsumoto, K., "Organic Synthesis under High Pressure II," *Synthesis*, (1985), 999-1027.
McDougal et al., "Asymmetric Morita-Baylis-Hillman Reactions Catalyzed by Chiral Brønsted Acids," *J. Am. Chem. Soc.*, (2003), 125:12094-12095.
Meddour et al., "Observation of Enantiomers, Chiral by Virtue of Isotopic Substitution, through Deuterium NMR in a Polypeptide Liquid Crystal," *J. Am. Chem. Soc.*, (1994), 116:9652-9656.
Midland et al., "Asymmetric Reductions of Propargyl Ketones," *Tetrahedron*, (1984), 40:1371-1380.
Midland et al., "Asymmetric Reductions of Prochiral Ketones with *B*-3-Pinanyl-9-borabicyclo[3,3.1]nonane (Alpine-Borande) at Elevated Pressures," *J. Org. Chem.*, (1989) 54:159-165.
Mirza-Aghayan et al., "Ultrasound Irradiation Effects on the Asymmetric Michael Reaction," *Tetrahedron Asymmetry*, (1995), 6(11):2643-2646.
Northrup et al., "The First Direct and Enantioselective Cross-Aldol Reaction of Aldehydes," *J. Am. Chem. Soc.*, (2002) 124:6798-6799.
Parker et al., "Asymmetric Reduction. A Convenient Method for the Reduction of Alkynyl Ketones," *J. Org. Chem.*, (1996) 61:3214-3217.

(Continued)

*Primary Examiner*—Brian J Davis
(74) *Attorney, Agent, or Firm*—Antoinette F. Konski; Foley & Lardner LLP

(57) ABSTRACT

This invention is directed to a method of performing a stereoselective reaction without use of a solvent comprising contacting a reactant with a chiral reagent under sonication conditions to form an excess of an enantiomer.

38 Claims, No Drawings

OTHER PUBLICATIONS

Pihko et al., "Effect of Additives on the ProlineCatalyzed Ketone-Aldehyde Aldol Reactions," *Tetrahedron*, (2006) 62:317-328.

Poisson et al., "Organocatalytic enantioselective protonation of silyl enolates mediated by cinchona alkaloids and a latent source of HF," *Angew. Chem. Int. Ed.*, (2007) 46:7090-7093.

Suslick et al., "Sonochemistry and Sonocatalysis of Iron Carbonyls," *J. Am. Chem. Soc.*, (1981), 103:7342-7344.

Suslick et al., "Sonochemistry and Sonocatalysis of Metal Carbonyls," *J. Am. Chem. Soc.*, (1983), 105:5781-5785.

Suslick et al., "Sonochemistry," *Science*, (1990), 247:1439-1445.

Suslick et al., "The Sonochemical Hot Spot," *J. Am. Chem. Soc.*, (1986), 108:5641-5642.

Thayumanavan et al., "Amine-Catalyzed Direct DielsAlder Reactions of αβ-Unsaturated Ketones with Nitro Olefins," *Tetrahedron Lett.*, (2002), 43:3817-3820.

Tietze et al., "Intermolecular Hetero-Diels-Alder Reactions of Enamino Ketones at High Pressure. The First Significant Pressure-Induced Diastereoselectivity in Organic Transformations," *J. Am. Chem. Soc.*, (1988), 110:4065-4066.

Trost et al., "Direct asymmetric aldol reactions of acetone using bimetallic zinc catalysts," *Org. Lett.*, (2001) 3(16):2497-2500.

Tsukinoki et al., "Preparation of benzyl-.alpha.-D1-alcohol by reduction of benzaldehyde with Raney alloys in an alkaline deuterium oxide solution," *Journal of Labelled Compounds and Radiopharmaceuticals*, (1993), 33(10):987-90.

Tuncay et al., "Ultrasound Promoted Hypervalent Iodine Reactions: α-Tosyloxylation of Ketones with [Hydroxy(Toxyloxy)Iodo]Benzene," *Tetrahedron Lett.*, (1992), 33, 7647-7650.

Wang et al., "An Efficient Catalytic Asymmetric Epoxidation Method," *J. Am. Chem. Soc.*, (1997) 119(46):11224-11235.

West et al., "A Mechanistic Probe for Asymmetric Reactions: Deuterium Isotope Effects at Enantiotopic Groups," *J. Am. Chem. Soc.*, (2008), 130:7816-7817.

Yamamoto et al., "Aldol Reaction of Silyl Enol Ethers Under Neutral Conditions," *J. Am. Chem. Soc.* (1983), 105:6963-6965.

Zeynizadeh et al, "Reduction of carbonyl compounds with NaBH4 under ultrasound irradiation and conditions," Zeitschrift fuer Naturforschung,B: *Chemical Sciences*, (2004), 59(6):704-710.

Zhang et al., "Enantioselective Epoxidation of Unfunctionalized Olefins Catalyzed by (Salen)manganese Complexes," *J. Am. Chem. Soc.*, (1990) 112:2801-2803.

\* cited by examiner

GENERAL METHOD FOR INCREASING STEREOSELECTIVITY IN STEREOSELECTIVE REACTIONS

CROSS-REFERENCE TO RELATED APPLICATIONS

This application claims the benefit under 35 U.S.C. §119 (e) of U.S. Provisional Patent Application No. 61/016,297 filed on Dec. 21, 2007, which is hereby incorporated by reference in its entirety.

FIELD OF THE INVENTION

This invention is directed to a method of performing a stereoselective reaction, such as reduction of an aldehyde, without the use of organic solvents, wherein the reactants are sonicated.

BACKGROUND OF THE INVENTION

Throughout this application, patent and technical literature may be referred to by a Roman numeral, the full bibliographic citations for which are found immediately preceding the claims. This information as well as the documents identified in the specification are provided to more fully describe the state of the art to which this invention pertains. These disclosures are incorporated by reference into the specification.

Stereoselective reactions are essential for the pharmaceutical industry. Since 1988, the FDA has required that the enantiomeric composition of all drugs having stereocenters be known. Often times, the reactions used to establish chirality at one or more centers are not stereoselective or not as stereoselective as would be desired. This results in costly purification steps. It is contemplated that the use of the technique described herein could eliminate purification steps, limit the environmental impact associated with solvent usage in purification steps, and be general in its application to most stereoselective reactions.

The exclusion of organic solvents would be advantageous as most organic solvents are dangerous for a variety of reasons. For example, solvents can be flammable or highly flammable, depending on their volatility. Many solvents can lead to a sudden loss of consciousness if inhaled in large amounts. Methanol can cause internal damage to the eyes, including permanent blindness. The commonly used solvent, diethyl ether, has an exceptionally low autoignition temperature which greatly increases the fire risk associated with this solvent. In addition, commonly used ethers such as diethyl ether, tetrahydrofuran (THF) and diisopropyl ether, form highly explosive organic peroxides upon exposure to oxygen and light. When sufficient peroxides have formed, they can form a shock sensitive solid, and when this solid is formed at the mouth of the bottle, turning the cap may provide sufficient energy for the peroxide to detonate. In addition, if the solvent is concentrated after the completion of a reaction, detonation can occur without warning.

In addition to the dangerous laboratory hazards above, environmental and heath issues arise from spills or leaks of solvents that reach the underlying soil. Since solvents readily migrate substantial distances, the creation of widespread soil contamination is not uncommon; there may be about 5000 sites worldwide that have major subsurface solvent contamination; this is particularly a health risk if aquifers are affected. Some solvents including chloroform and benzene are carcinogenic, and many others can damage internal organs like the liver, the kidneys, or the brain.

Disclosed herein are methods for alleviating the need for solvents in asymmetric reactions. Such methods rely on the utilization of ultrasonic irradiation. Currently, the overwhelming majority of reports detailing the effects of ultrasonic irradiation upon chemistry are concerned with heterogeneous reactions. In these studies, ultrasound has been applied simply as a means to increase the area of contact between reactants or a reactant and catalyst.[i-iii] To our knowledge, only three successful uses of ultrasound in homogeneous chemistry exist.[iv-vii] H. C. Brown has shown an increased yield in the hydroboration of alkenes using a number of organoboranes were increased to nearly quantitative amounts while reaction times were shortened considerably under ultrasonic irradiation.[vi]

The principal conclusion from preliminary work of the Suslick group at the University of Illinois, Urbana-Champaign performed in the 1980s is that cavitation is responsible for many of the phenomena observed in sonochemistry.[viii] Cavitations are derived from the nucleation of bubbles at weak spots in liquid structure and the subsequent collapse of these low density regions. The collapse of the bubble is thought to generate what are known as 'hot spots'. High local pressures and temperatures are thought to be associated with these 'hot spots'. Local temperatures on the order of 5000 K are thought to be generated in the immediate vicinity of cavitations.[ix] Estimates of pressures range from 1-10 Kbar.[x] Recently, pressure broadening studies upon sonoluminescing bubbles have estimated intracavity pressures have been measured between 1.6 and 3.7 Kbar.[xi]

The Evans-Polanyi equation illustrates how pressure affects rate (equation 1). For most bimolecular reactions, the volume of activation ($\Delta V^{\neq}$) is negative, which translates into a rate enhancement upon the application of pressure.[xii,xiii]

$$(\partial \ln k/\partial P)_T = -\Delta V^{\neq}/RT \tag{1}$$

If two competing pathways are operative in a reaction, such as endo/exo competition in Diels-Alder reactions, antil syn competition in aldol reactions, and Rel Si competition in stereoselective reductions, then the pathway with the largest negative volume of activation (smallest transition state volume) will be accelerated to a greater degree than the pathway with the smaller negative volume of activation (larger transition state volume).[xiv,xv] Stereochemical outcomes are often thought to be dominated by steric interactions. This principle is demonstrated in the Felkin-Anh model[xvi] and has been quantitatively shown in the DIP-Cl reduction of prochiral ketones.[xvii] For different reasons (secondary orbital overlap), the endo transition state in the Diels-Alder reaction is often preferred over the exo transition state. However, in the hetero-Diels-Alder reaction, the exo-product is preferred. This is perhaps due to overwhelming steric occlusion that occurs in the endo-transition structure as a result of substitution of the diene. Such a model makes sense, given that the application of high static pressures drastically increase diastereoselectivity.[xviii] The reversal in stereoselectivity observed in the Mukaiyama aldol reaction has been rationalized by the pressure-induced preference for a more compact boat-like transition structure over the typical Zimmerman transition structure.[xix] The results reported herein are consonant with reports that the application of high static pressures (6000 Kbar) drastically improve stereoselection in Alpine Borane reductions.

In order to decrease both the heath and environmental risks associated with the use of organic solvents, chemists must come up with alternative methods for organic synthesis. Any alternative methods may either improve or maintain the yield or selectivity of a reaction which utilizes significant amounts of organic solvents. The use of solvent-free methods would greatly decrease these risks and allow for environmentally friendly or "green" chemistry.

SUMMARY OF THE INVENTION

The methods described herein are directed to stereoselective reactions without the use of organic solvents. It is contemplated that the methods of the invention will reduce the costs associated with producing high-value-added chemicals, especially in the pharmaceutical industry. The methods of the invention will provide more rapid processing of feedstock, reduce solvent usage in purification steps, and use less energy and manpower in purification.

In one aspect, the present invention discloses a method of performing a stereoselective reaction without use of an organic solvent comprising sonicating a reactant in the presence of a chiral reagent to form a product; provided that the chiral reagent is not covalently bonded to the reactant; and further provided that the chiral reagent is not N-benzyl-1-hydroxy-N,N-dimethyl-1-phenylpropan-2-aminium bromide. It is contemplated that the methods of the invention will increase stereoselectivity and/or yield compared to reactions that are performed neat without sonication.

In another aspect, the present invention discloses a method of performing a stereoselective reaction without use of a solvent comprising contacting a reactant with a chiral reagent under sonication conditions to form an excess of an enantiomer.

In yet another aspect, the present invention discloses a method of performing a stereoselective reaction without use of a solvent comprising contacting a reactant with a chiral reagent under sonicating conditions to form an excess of an enantiomer, wherein the reactant is of formula I:

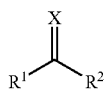

I wherein:

X is selected from the group consisting of O, S, and $NR^3$;

$R^1$ and $R^2$ are independently selected from the group consisting of hydrogen, deuterium, halo, nitro, cyano, alkyl, substituted alkyl, alkenyl, substituted alkenyl, alkynyl, substituted alkynyl, haloalkyl, alkoxy, substituted alkoxy, cycloalkyl, substituted cycloalkyl, aryl, substituted aryl, heteroaryl, substituted heteroaryl, amino, substituted amino, aminoacyl, acylamino, alkylthio, and substituted alkylthio, with the proviso that $R^1$ is not identical to $R^2$;

$R^3$ is selected from the group consisting of hydrogen, alkyl, substituted alkyl, aryl, substituted aryl, —S(O)$R^4$, —C(O)$R^4$, and —NR$^5$R$^5$;

$R^4$ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, and substituted amino;

each $R^5$ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both $R^5$ can be attached with an optional C(O) to form a heterocycle;

provided that the chiral reagent is not covalently bonded to the reactant; and further provided that the chiral reagent is not N-benzyl-1-hydroxy-N,N-dimethyl-1-phenylpropan-2-aminium bromide.

In one aspect, the present invention discloses a method of performing a stereoselective reaction without use of a solvent comprising contacting a reactant with a chiral reagent under sonication conditions to form an excess of an enantiomer, wherein the reaction is a reduction of an aldehyde, ketone, alpha-haloketone, aldimine, imine or alpha-haloimine; provided that the chiral reagent is not covalently bonded to the reactant; and further provided that the chiral reagent is not N-benzyl-1-hydroxy-N,N-dimethyl-1-phenylpropan-2-aminium bromide.

In yet another aspect, the present invention discloses a method of reducing an aryl-d-aldehyde without the use of a solvent comprising of sonicating the aryl-d-aldehyde in the presence of B-isopinocampheyl-9-borabicyclo[3.3.1]nonane to form an aryl-d-methanol. In still yet another aspect, the present invention discloses a method of reducing 2,4,6-trimethyl-d-benzaldehyde without the use of a solvent comprising sonicating 2,4,6-trimethyl-d-benzaldehyde in the presence of B-isopinocampheyl-9-borabicyclo[3.3.1]nonane (Alpine Borane®) to form 2,4,6-trimethylphenyl-d-methanol.

DETAILED DESCRIPTION OF THE INVENTION

Before the methods are described, it is to be understood that the invention is not limited to the particular methodologies, protocols and reagents described, as these may vary. It is also to be understood that the terminology used herein is intended to describe particular embodiments of the present invention, and is in no way intended to limit the scope of the present invention as set forth in the appended claims.

1. Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety. Nothing herein is to be construed as an admission that the invention is not entitled to antedate such disclosure by virtue of prior invention.

It must be noted that as used herein and in the appended claims, the singular forms "a," "an," and "the" include plural references unless the context clearly dictates otherwise.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5 hydrogens replaced with substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, sulfonylamino, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are defined herein. In some implementations, the alkyl has 1 to 3 of the aforementioned groups. In other implementations, the alkyl has 1 to 2 of the aforementioned groups.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) or (—$CH(CH_3)CH_2$—), and the like.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminocarbonyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some implementations, the alkylene has 1 to 2 of the aforementioned groups. It is to be noted that when the alkylene is substituted by an oxo group, 2 hydrogens attached to the same carbon of the alkylene group are replaced by "=O".

"Alkoxy" refers to the group —O-alkyl, wherein alkyl is as defined herein. Alkoxy includes methoxy, ethoxy, n-propoxy, isopropoxy, n-butoxy, t-butoxy, sec-butoxy, n-pentoxy, and the like.

"Substituted alkoxy" refers to the group —O-(substituted alkyl), wherein substituted alkyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{20}C(O)$alkyl, —$NR^{20}C(O)$substituted alkyl, —$NR^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, where one of $R^{21}$ and $R^{22}$ is sulfonyl, and wherein $R^{21}$ and $R^{22}$ are optionally joined together with the nitrogen bound thereto to form a heterocyclic or substituted heterocyclic group, provided that $R^{21}$ and $R^{22}$ are not both hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, sulfonyl, substituted heteroaryl, heterocyclic, and substituted heterocyclic are as defined herein. When $R^{21}$ is hydrogen and $R^{22}$ is alkyl, the substituted amino group is sometimes referred to herein as "alkylamino." When $R^{21}$ and $R^{22}$ are alkyl, the substituted amino group is sometimes referred to herein as "dialkylamino." When referring to a monosubstituted amino, it is meant that either $R^{21}$ or $R^{22}$ is hydrogen, but not both. When referring to a disubstituted amino, it is meant that neither $R^{21}$ nor $R^{22}$ is hydrogen.

"Aminocarbonyl" refers to the group —C(O)NR$^{21}$R$^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{21}$R$^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{20}$C(O)NR$^{21}$R$^{22}$, wherein $R^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NR$^{20}$C(S)NR$^{21}$R$^{22}$, wherein $R^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR$^{21}$R$^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$—NR$^{21}$R$^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR$^{21}$R$^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic; $R^{21}$ and $R^{22}$ are optionally joined together with the nitrogen bound thereto to form a heterocyclic or substituted heterocyclic group; and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{20}$—SO$_2$NR$^{21}$R$^{22}$, wherein $R^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{30}$)NR$^{31}$R$^{32}$, wherein R$^{31}$ and R$^{32}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{31}$ and R$^{32}$ are optionally joined together with the nitrogen bound thereto to form a heterocyclic or substituted heterocyclic group. R$^{30}$ is selected from the group consisting of hydrogen, alkyl, substituted alkyl, alkenyl, substituted alkenyl, alkynyl, substituted alkynyl, cycloalkynyl, substituted cycloalkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, nitro, nitroso, hydroxy, alkoxy, cyano, acyl, —SO$_2$-alkyl and —SO$_2$-substituted alkyl, wherein alkyl, substituted alkyl, alkenyl, substituted alkenyl, alkynyl, substituted alkynyl, cycloalkynyl, substituted cycloalkynyl, cycloalkyl, substituted cycloalkyl, cycloalkenyl, substituted cycloalkenyl, aryl, substituted aryl, heteroaryl, substituted heteroaryl, heterocyclic, substituted heterocyclic, nitro, nitroso, hydroxy, alkoxy, and cyano are as defined herein.

"Aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic provided that the point of attachment is through an atom of the aromatic aryl group. For example, 1,2,3,4-tetrahydronaphthalen-5-yl, 9H-fluoren-2-yl, and the like. Preferred aryl groups include phenyl and naphthyl.

"Substituted aryl" refers to aryl groups having 1 to 5 hydrogens replaced with substituents independently selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, —SO$_3$H, sulfonyl, sulfonyloxy, thioacyl, thiol, alkylthio, and substituted alkylthio, wherein said substituents are as defined herein. In some implementations, the aryl has 1 to 3 of the aforementioned groups. In other implementations, the aryl has 1 to 2 of the aforementioned groups. In some implementations, substituted aryl includes compounds containing oxo substituent in the non-aromatic ring fused to the aryl group. For example, 1-oxo-indan-4-yl, wherein the point of attachment is through the phenyl ring.

"Aryloxy" refers to the group —O-aryl, wherein aryl is as defined herein, including, by way of example, phenoxy, naphthoxy, and the like.

"Substituted aryloxy" refers to the group —O-(substituted aryl), wherein substituted aryl is as defined herein.

"Arylthio" refers to the group —S-aryl, wherein aryl is as defined herein. In other implementations, sulfur may be oxidized to —S(O)— or —SO$_2$— moieties. Sulfoxides may exist as one or more stereoisomers, e.g. methylsulfinylethane is a chiral molecule having two enantiomeric forms, R and S.

"Substituted arylthio" refers to the group —S-(substituted aryl), wherein substituted aryl is as defined herein. In other implementations, sulfur may be oxidized to —S(O)— or —SO$_2$— moieties. The sulfoxide may exist as one or more stereoisomers.

"Alkenyl" refers to straight chain or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified by vinyl, allyl, and but-3-en-1-yl. Included within this term are the cis and trans isomers or mixtures of these isomers.

"Substituted alkenyl" refers to alkenyl groups having from 1 to 3 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thioacyl, thiol, alkylthio, and substituted alkylthio, wherein said substituents are as defined herein and with the proviso that any hydroxy substitution is not attached to a vinyl (unsaturated) carbon atom. In some implementations, the alkenyl has 1 to 2 of the aforementioned groups.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic —C≡—C— unsaturation. Examples of such alkynyl groups include acetylenyl (—C≡—CH), and propargyl (—CH$_2$C≡CH).

"Substituted alkynyl" refers to alkynyl groups having from 1 to 3 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thioacyl, thiol, alkylthio, and substituted alkylthio, wherein said substituents are as defined herein and with the proviso that any hydroxy or thiol substitution is not attached to an acetylenic carbon atom. In some implementations, the alkynyl has 1 to 2 of the aforementioned groups.

"Alkynyloxy" refers to the group —O-alkynyl, wherein alkynyl is as defined herein. Alkynyloxy includes, by way of example, ethynyloxy, propynyloxy, and the like.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the groups —NR—C(O)O-alkyl, —NR—C(O)O-substituted alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic, wherein R is alkyl or hydrogen and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 13 carbon atoms having single or multiple cyclic rings including fused, bridged, and spiro ring systems. Examples of cycloalkyl groups include adamantyl, cyclopropyl, cyclobutyl, cyclopentyl, cyclooctyl, and the like. One or more rings fused to the cycloalkyl group can be aromatic, provided that the point of attachment is through the non-aromatic ring, e.g. 9H-fluoren-9-yl, 1,2,3,4-tetrahydronaphthalen-2-yl, and the like.

"Cycloalkenyl" refers to non-aromatic cyclic alkyl groups of from 3 to 10 carbon atoms having single or multiple rings and having at least one double bond and preferably from 1 to 2 double bonds.

"Cycloalkynyl" refers to non-aromatic cycloalkyl groups of from 7 to 12 carbon atoms having single or multiple rings and having at least one triple bond.

"Cycloalkylene" refers to divalent cycloalkyl groups, wherein cycloalkyl is as defined herein.

"Substituted cycloalkylene" refers to cycloalkylene group having from 1 to 3 hydrogens replaced with substituents selected from the group consisting of alkyl, substituted alkyl, alkoxy, substituted alkoxy, acyl, acylamino, acyloxy, amino, substituted amino, aminocarbonyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are as defined herein. In some implementations, the alkylene has 1 to 2 of the aforementioned groups. It is to be noted that when the cycloalkylene is substituted by an oxo group, 2 hydrogens attached to the same carbon of the cycloalkylene group are replaced by "=O".

"Substituted cycloalkyl," "substituted cycloalkenyl," and "substituted cycloalkynyl" refer to a cycloalkyl, cycloalkenyl, or cycloalkynyl group having from 1 to 5 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, —SO₃H, sulfonyl, sulfonyloxy, thioacyl, thiol, alkylthio, and substituted alkylthio, wherein said substituents are as defined herein, provides that any hydroxy or thiol substitution is not attached to an unsaturated carbon atom. In some implementations, the cycloalkyl or cycloalkenyl has 1 to 3 of the aforementioned groups.

"Cycloalkoxy" refers to —O-cycloalkyl.

"Substituted cycloalkoxy" refers to —O-(substituted cycloalkyl).

"Cycloalkylthio" refers to —S-cycloalkyl. In other implementations, sulfur may be oxidized to —S(O)— or —SO₂— moieties. The sulfoxide may exist as one or more stereoisomers.

"Substituted cycloalkylthio" refers to —S-(substituted cycloalkyl). In other implementations, sulfur may be oxidized to —S(O)—, or —SO₂— moieties. The sulfoxide may exist as one or more stereoisomers.

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl. In other implementations, sulfur may be oxidized to sulfinyl or sulfonyl moieties. The sulfoxide may exist as one or more stereoisomers.

"Substituted cycloalkenylthio" refers to —S-(substituted cycloalkenyl). In other implementations, sulfur may be oxidized to —S(O)— or —SO$_2$— moieties. The sulfoxide may exist as one or more stereoisomers.

"Guanidino" refers to the group —NHC(=NH)NH$_2$.

"Substituted guanidino" refers to the group —NR$^{33}$C(=NR$^{33}$)N(R$^{33}$)$_2$, wherein each R$^{33}$ independently is selected from the group consisting of hydrogen, alkyl, substituted alkyl, aryl, substituted aryl, heteroaryl, substituted heteroaryl, heterocyclic, and substituted heterocyclic; two R groups attached to a common guanidino nitrogen atom are optionally joined together with the nitrogen bound thereto to form a heterocyclic or substituted heterocyclic group, provided that at least one R is not hydrogen; and said substituents are as defined herein.

"Halo" or "halogen" refers to fluoro, chloro, bromo, and iodo and is preferably fluoro or chloro.

"Haloalkyl" refers to alkyl groups substituted with 1 to 5, 1 to 3, or 1 to 2 halo groups, wherein alkyl and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl or furyl) or multiple condensed rings (e.g., indolizinyl or benzothienyl), wherein the condensed rings may or may not be aromatic and/or contain a heteroatom, provided that the point of attachment is through an atom of the aromatic group containing the heteroatom. In one implementation, the nitrogen and/or sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5 substituents selected from the group consisting of the same group of substituents defined for substituted aryl. In some implementations, the heteroaryl has 1 to 3 of the aforementioned groups. In other implementations, the heteroaryl has 1 to 2 of the aforementioned groups.

"Heteroaryloxy" refers to —O-heteroaryl.

"Substituted heteroaryloxy" refers to the group —O-(substituted heteroaryl).

"Heteroarylthio" refers to the group —S-heteroaryl. In other implementations, sulfur may be oxidized to —S(O)— or —SO$_2$— moieties. The sulfoxide may exist as one or more stereoisomers.

"Substituted heteroarylthio" refers to the group —S-(substituted heteroaryl). In other implementations, sulfur may be oxidized to —S(O)— or —SO$_2$— moieties. The sulfoxide may exist as one or more stereoisomers.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In one implementation, the nitrogen and/or sulfur atom(s) of the heterocyclic group are optionally oxidized to provide for the N-oxide, —S(O)—, or —SO$_2$— moieties.

"Substituted heterocyclic," "substituted heterocycloalkyl," and "substituted heterocyclyl" refer to heterocyclyl groups that are substituted with from 1 to 5 of the same substituents as defined for substituted cycloalkyl. In some implementations, the heterocyclyl has 1 to 3 of the aforementioned groups.

"Heterocyclyloxy" refers to the group —O-heterocyclyl.

"Substituted heterocyclyloxy" refers to the group —O-(substituted heterocyclyl).

"Heterocyclylthio" refers to the group —S-heterocyclyl. In other implementations, sulfur may be oxidized to —S(O)— or —SO$_2$— moieties. The sulfoxide may exist as one or more stereoisomers.

"Substituted heterocyclylthio" refers to the group —S-(substituted heterocyclyl). In other implementations, sulfur may be oxidized to —S(O)— or —SO$_2$— moieties. The sulfoxide may exist as one or more stereoisomers.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitro" refers to the group —NO$_2$.

"Nitroso" refers to the group —NO.

"Oxo" refers to the atom (=O).

"Sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, and —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thioxo" refers to the atom (=S).

"Alkylthio" refers to the group —S-alkyl, wherein alkyl is as defined herein. In other implementations, sulfur may be oxidized to —S(O)—. The sulfoxide may exist as one or more stereoisomers.

"Substituted alkylthio" refers to the group —S-(substituted alkyl), wherein substituted alkyl is as defined herein. In other implementations, sulfur may be oxidized to —S(O)—. The sulfoxide may exist as one or more stereoisomers.

"Aldehyde" refers to H—C(O)H, alkyl-C(O)H, substituted alkyl-C(O)H, alkenyl-C(O)H, substituted alkenyl-C(O)H, alkynyl-C(O)H, substituted alkynyl-C(O)H, cycloalkyl-C(O)H, substituted cycloalkyl-C(O)H, cycloalkenyl-C(O)H, substituted cycloalkenyl-C(O)H, aryl-C(O)H, substituted aryl-C(O)H, heteroaryl-C(O)H, substituted heteroaryl-C(O)H, heterocyclic-C(O)H, and substituted heterocyclic-C(O)H, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. In some embodiments, the aldehyde is a deuterated aldehyde wherein the aldehyde hydrogen has been replaced with a deuterium (—C(O)—$^2$H).

"Ketone" refers to R'—C(O)—R', wherein each R' is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, or substituted heterocyclic.

"Alpha-haloketone" refers to R'—C(O)—C(X)HR', wherein each R' is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, or substituted heterocyclic and X is a halogen.

"Aldimine" refers to H—C(NR')H, alkyl-C(NR')H, substituted alkyl-C(NR')H, alkenyl-C(NR')H, substituted alkenyl-C(NR')H, alkynyl-C(NR')H, substituted alkynyl-C(NR')H, cycloalkyl-C(NR')H, substituted cycloalkyl-C(NR')H, cycloalkenyl-C(NR')H, substituted cycloalkenyl-C(NR')H, aryl-C(NR')H, substituted aryl-C(NR')H, heteroaryl-C(NR')H, substituted heteroaryl-C(NR')H, heterocyclic-C(NR')H, and substituted heterocyclic-C(NR')H, wherein R' is alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Imine" refers to R'—C(NR')—R', wherein each R' is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, or substituted heterocyclic.

"Alpha-haloimine" refers to R'—C(NR')—C(X)HR', wherein each R' is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, or substituted heterocyclic and X is a halogen.

"Alcohol" refers to a compound comprising an —OH group.

"Aryl-d-aldehyde" refers to a compound of the formula aryl-C(O)—$^2$H.

"Aryl-d-methanol" refers to a compound of the formula aryl-CH(OH)—$^2$H.

"Stereoisomer" and "stereoisomers" refer to compounds that have same atomic connectivity but different atomic arrangement in space. Stereoisomers include cis-trans isomers, E and Z isomers, enantiomers, and diastereomers.

As used herein, the term "enantiomeric excess" is intended to refer to an excess of one enantiomer over the other. The term "enantiomer" refers to either of a pair of optical isomers that are mirror images of each other.

As used herein, the term "sonication" is intended to mean the act of applying ultrasonic energy. The ultrasonic energy can be applied using an ultrasonic bath or an ultrasonic probe. As used for chemistry, the typical frequency range is from about 40 kHz to about 270 kHz, or alternatively, from about 20 kHz to about 100 kHz. The term "sonication conditions" refers to subjecting a chemical reaction to sonication.

"Alpine Borane®" is intended to mean B-isopinocampheyl-9-borabicyclo[3.3.1]nonane. Alpine Borane® is a commercially available (Sigma, www.sigmaaldrich.com) chiral reducing agent used primarily for the asymmetric reduction of carbonyl compounds. Other chiral boron based reducing agents include B-chlorodiisopinocampheylborane, B-methoxydiisopinocampheylborane, NB-enantride™ (9-BBN-nopol benzyl ether adduct), and the like.

As used herein, the term "stereoselective reaction" is intended to refer to a chemical reaction in which of two or more possible stereoisomeric products only one predominates. In the methods disclosed herein, the stereoselective reaction involves the utilization of a "chiral reagent". A "chiral reagent" is a reagent that contains at least one center of chirality and which provides, upon reaction with the reactant, a chiral product. As used herein, the term "product" is intended to refer to the product of the reaction between the reactant and the chiral reagent. One or more additional reagents may also be involved in the stereoselective reaction. Various chiral reagents are known to those of skill in the art, and they can be selected based on the desired stereoselective reaction and reactant. For example, chiral reagents which are contemplated to be suitable for inclusion in the methods disclosed herein are boron reagents, such as those available from BASF Corporation (New Jersey, USA) including, but not limited to, diisopinocampheylchloroborane, Alpine Borane®, alkyl or aryl oxazaborolidines, and the like.

As used herein, the term "contacting" is intended to refer to allowing reagents and reactants to react with each other in a reaction vessel.

As used herein, the term "reduction" is intended to mean the transfer of a hydride from one molecule to another, resulting in a carbon with a lower oxidation state.

As used herein, the term "alkylation" is intended to mean the transfer of an alkyl or substituted alkyl group from one molecule to another. The alkyl group may be transferred as an alkyl carbocation, a free radical, a carbanion or a carbene (or their equivalents).

As used herein, the term "cyclization" is intended to mean the formation of one or more rings in a reagent.

As used herein, the term "epoxidation" is intended to refer to the chemical transformation of an alkene to an epoxide.

As used herein, the term "aldol addition" is intended to refer to the nucleophilic addition of an enolate to a carbonyl group to form a β-hydroxy carbonyl.

As used herein, the term "halogenation" is intended to refer to a chemical reaction that incorporates a halogen atom into a molecule.

As used herein, the term "Diels-Alder reaction" is intended to refer to a cycloaddition reaction between a conjugated diene and a substituted alkene to form a substituted cyclohexene. The term "cycloaddition" is intended to refer to a pericyclic chemical reaction, in which two π bonds are lost and two σ bonds are gained.

As used herein, the term "Baylis-Hillman" is intended to refer to the reaction between an aldehyde and an α,β-unsaturated electron-withdrawing group catalyzed by an amine to give an allylic alcohol. In using such reactions in the methods disclosed herein, it is contemplated that the amine would be chiral to act as a chiral reagent.

As used herein, the term "protonation" is intended to mean the transfer of a proton from a proton source to a molecule. In using such reactions in the methods disclosed herein, it is contemplated that the proton source would act as the chiral reagent.

As used herein, the term "solvent" is intended to mean a liquid which contains at least one substance capable of bringing at least one other substance into solution. Thus, the solvent medium might be at least one organic and/or inorganic solvent or can alternatively be an alkaline or acid solution. Examples of organic solvents include tetrahydrofuran, diethyl ether, methyl tert-butyl ether, dioxane, hexane, pentane, benzene, toluene, and methylene chloride. In addition, ionic liquids are included by the scope of the reactions disclosed herein. Examples of ionic liquids include those derived from methylimidazolium and pyridinium ions, such as 1-butyl-3-methylimidazolium tetrafluoroborate and 1-butyl-4-methylpyridinium hexafluorophosphate, and the like.

In the examples and elsewhere in the specification, abbreviations have the following meanings:

| | |
|---|---|
| THF = | tetrahydrofuran |
| mL = | milliliter |
| g = | gram |
| mmol = | millimole |
| M = | molar |
| kHz = | kilohertz |
| NMR = | nuclear magnetic resonance |
| neat = | solvent-free |
| Et = | ethyl |
| Ph = | phenyl |
| Me = | methyl |

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are an infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

2. Methods of the Inventions

It is contemplated that by sonicating the reactants in a stereoselective reaction, there is no longer a need or alternatively a significantly reduced need for using organic solvents. Also contemplated by this invention, is that by sonicating the reactants, stereoselectivity and/or yield is also improved. Overcoming poor stereoselectivity usually requires co-crystallization with a chiral adduct, kinetic resolution of the stereoisomers, or separation-based strategies such as chiral high-performance liquid chromatography (HPLC). Typically, stereoselection in a given reaction is enhanced by performing reactions at lower temperatures. Often, as in the case of Alpine Borane® reductions, this is not possible because the reducing agent is not reactive at lower temperatures. Another source of increased energy demand for a particular reaction can be attributed to the desired substrate rather than reactant. The more sterically demanding the substrate, the more energy is required. However, heating a reaction can be detrimental as temperature and selectivity often have an inverse relationship. In addition to steric factors, electronics can cause a reaction to become less efficient. Often, aryl carbonyl compounds are less reactive than alkyl carbonyl compounds due to conjugation. It is contemplated that sonication can be used to overcome the energy boundaries for many stereoselective reactions, whatever the reason.

Where this process can be used in conjunction with cooling, it is contemplated to further enhance stereoselectivity and/or yield. The disadvantage that was eliminated was the lower-than-desired reactivity of the Alpine Borane® reduction under solvent-free conditions, resulting in less than acceptable yield and enantiomeric excess. Many reactions, such as reductions, alkylations, epoxidations, cyclizations, aldol additions, halogenations, Diels-Alder reactions, cycloadditions, Baylis-Hillman reactions and protonations, are of limited value with a given substrate because of the inherent limitations of the catalyst or reagent. Sonication of stereoselective reactions should confer higher stereoselectivity in most reactions, since most stereoselective reactions have negative volumes of reactions.

In one aspect, the present invention discloses a method of performing a stereoselective reaction without use of a solvent comprising contacting a reactant with a chiral reagent under sonication conditions to form an excess of an enantiomer; provided that the chiral reagent is not covalently bonded to the reactant; and further provided that the chiral reagent is not N-benzyl-1-hydroxy-N,N-dimethyl-1-phenylpropan-2-aminium bromide. Included within the scope of the present invention are various reactions, such as reductions, alkylations, epoxidations, cyclizations, aldol additions, halogenations, Diels-Alder reactions, cycloaddition reactions, Baylis-Hillman reactions and protonations. Alternatively, the reaction is a reduction of an aldehyde, ketone, alpha-haloketone, aldimine, imine and alpha-haloimine. In one embodiment, the stereoselective reaction is a reduction. In another embodiment, the reduction is the reduction of an aldehyde.

In one embodiment, the method disclosed herein is performed using a reduced amount of solvent thereby increasing the concentration of reactant compared to the typical reaction conditions.

In yet another aspect, the present invention discloses a method of performing a stereoselective reaction without use of an organic solvent comprising sonicating an aldehyde in the presence of Alpine Borane®. Specifically, the present invention discloses a method of reducing 2,4,6-trimethyl-d-benzaldehyde without the use of a solvent comprising of sonicating 2,4,6-trimethyl-d-benzaldehyde in the presence of Alpine Borane® to form 2,4,6-trimethylphenyl-d-methanol.

It is contemplated that any chiral reagent can be used in the methods disclosed herein. For example, boron reagents, such as those available from BASF Corporation (New Jersey, USA) including, but not limited to, diisopinocampheylchloroborane, Alpine Borane®, alkyl or aryl oxazaborolidines, and the like.

In one embodiment, quaternary ammonium chiral reagents are not included within the scope of the claims. In another embodiment, ephedrine or ephedrine derivatives are not chiral reagents included within the scope of the claims. Ephedrine derivatives include substituted ephedrine and pseudoephedrine compounds, as well as the salts thereof. In one embodiment, is not N-benzyl-1-hydroxy-N,N-dimethyl-1-phenylpropan-2-aminium bromide.

Typically, asymmetric reactions take place in solution using an ethereal or halogenated organic solvent. The use of these organic solvents can be a source of heath and safety hazards. In another aspect, the present invention discloses a method of performing a stereoselective reaction without use of a solvent comprising contacting a reactant with a chiral reagent under sonication conditions to form an excess of an enantiomer, wherein the solvent is one or more of tetrahydrofuran, diethyl ether, methyl tert-butyl ether, dioxane, hexane, pentane, benzene, toluene, methylene chloride, combinations thereof, or other suitable organic solvents.

It is contemplated that any means for sonicating can be used in the methods disclosed herein, including, but not limited to an ultrasonic bath or an ultrasonic probe. Various powers and frequencies are possible using different sonicators. In one embodiment, the sonication conditions comprise sonicating at a power of from about 24 Watts to about 240 Watts. In a certain embodiment, the sonication conditions comprise sonicating at a power of about 80 Watts. In one embodiment, the sonication conditions comprise sonicating at a frequency of from about 40 kHz to about 270 kHz. In another embodiment, the sonication conditions comprise sonicating at a frequency of about 40 kHz.

Depending on the specific reaction being performed, various reaction temperatures can be employed in the methods disclosed herein. For example, in one embodiment, the sonication conditions comprise sonicating at a temperature of from about −78° C. to about 65° C. In some embodiments, the sonication conditions comprise sonicating at a temperature of from about −40° C. to about 40° C. In certain embodiments, the sonication conditions comprise sonicating at a temperature of from about 20° C. to about 40° C.

Employing the methods disclosed herein can result in the presence of one enantiomer in an enantiomeric excess greater than the enantiomeric excess in the corresponding reaction that does not employ sonication conditions. In some embodiments, the increase in enantiomeric excess is about 5%, or alternatively, about 10%, or alternatively, about 15%, or alternatively, about 20%, or alternatively, about 25%, or alternatively, about 30%, or alternatively, about 35%, or alternatively, about 40%, or alternatively, about 45%, or alternatively, greater than about 50%.

In addition, in some embodiments, the yield of the stereoselective reaction performed under sonication conditions is greater than the yield of the corresponding reaction that does not employ sonication conditions. In some embodiments, the increase in yield is about 5%, or alternatively, about 10%, or alternatively, about 15%, or alternatively, about 20%, or alternatively, about 25%, or alternatively, about 30%, or alternatively, about 35%, or alternatively, about 40%, or alternatively, about 45%, or alternatively, greater than about 50%.

In another aspect, the present invention discloses a method of performing a stereoselective reaction without use of a solvent comprising contacting a reactant with a chiral reagent under sonicating conditions to form an excess of an enantiomer, wherein the reactant is of formula I:

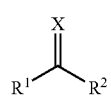

wherein:

X is selected from the group consisting of O, S, and $NR^3$;

$R^1$ and $R^2$ are independently selected from the group consisting of hydrogen, deuterium, halo, nitro, cyano, alkyl, substituted alkyl, alkenyl, substituted alkenyl, alkynyl, substituted alkynyl, haloalkyl, alkoxy, substituted alkoxy, cycloalkyl, substituted cycloalkyl, aryl, substituted aryl, heteroaryl, substituted heteroaryl, amino, substituted amino, aminoacyl, acylamino, alkylthio, and substituted alkylthio, with the proviso that $R^1$ is not identical to $R^2$;

$R^3$ is selected from the group consisting of hydrogen, alkyl, substituted alkyl, aryl, substituted aryl, —$S(O)R^4$, —$C(O)R^4$, and —$NR^5R^5$;

$R^4$ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, and substituted amino;

each $R^5$ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both $R^5$ can be attached with an optional C(O) to form a heterocycle;

provided that the chiral reagent is not covalently bonded to the reactant; and further provided that the chiral reagent is not N-benzyl-1-hydroxy-N,N-dimethyl-1-phenylpropan-2-aminium bromide.

In one embodiment, X is O. In another embodiment, X is S. In yet another embodiment, X is $NR^3$.

In one embodiment, $R^1$ and $R^2$ are independently selected from the group consisting of hydrogen, deuterium, alkyl, substituted alkyl, alkenyl, substituted alkenyl, alkynyl, substituted alkynyl, haloalkyl, cycloalkyl, substituted cycloalkyl, aryl, substituted aryl, heteroaryl, and substituted heteroaryl. In a certain embodiment, $R^1$ and $R^2$ are independently selected from the group consisting of deuterium, alkyl, substituted alkyl, alkynyl, substituted alkynyl, haloalkyl, aryl, and substituted aryl.

In yet another aspect, the present invention discloses a method of performing a stereoselective reaction without use of a solvent comprising contacting a reactant with a chiral reagent under sonicating conditions to form an excess of an enantiomer, wherein the reactant is of formula II:

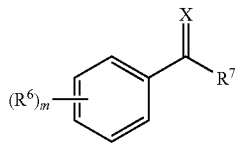

wherein:

X is selected from the group consisting of O, S, and $NR^3$;

$R^3$ is selected from the group consisting of hydrogen, alkyl, substituted alkyl, aryl, substituted aryl, —$S(O)R^4$, —$C(O)R^4$—$NR^5R^5$;

$R^4$ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino;

each $R^5$ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both $R^5$ can be attached with an optional C(O) to form a heterocycle;

each $R^6$ is independently selected from the group consisting of halo, nitro, cyano, hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino, aminoacyl, acylamino, alkylthio, substituted alkylthio, and acyl;

$R^7$ is selected from the group consisting of hydrogen, deuterium, alkyl, substituted alkyl, haloalkyl, cycloalkyl, substituted cycloalkyl, aryl, substituted aryl, heteroaryl and substituted heteroaryl; and m is an integer from 0 to 5.

In one embodiment of formula II, X is O.

In another embodiment of formula II, each $R^6$ is independently selected from the group consisting of alkyl and substituted alkyl; and m is an integer from 0 to 3.

In yet another embodiment of formula II, $R^7$ is selected from the group consisting of deuterium, alkyl and substituted alkyl.

In a certain embodiment of formula II, X is O; each $R^6$ is independently selected from the group consisting of alkyl and substituted alkyl; m is an integer from 0 to 3; and $R^7$ is selected from the group consisting of deuterium and alkyl.

In yet another aspect, the present invention discloses a method of performing a stereoselective reaction without use of a solvent comprising contacting a reactant with a chiral reagent under sonicating conditions to form an excess of an enantiomer, wherein the reactant is of formula III:

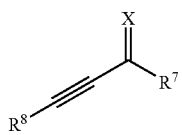

wherein:

X is selected from the group consisting of O, S, and $NR^3$;

$R^3$ is selected from the group consisting of hydrogen, alkyl, substituted alkyl, aryl, substituted aryl, —$S(O)R^4$, —$C(O)R^4$ and —$NR^5R^5$;

$R^4$ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino;

each $R^5$ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both $R^5$ can be attached with an optional C(O) to form a heterocycle;

$R^7$ is selected from the group consisting of hydrogen, deuterium, alkyl, substituted alkyl, haloalkyl, cycloalkyl, substituted cycloalkyl, aryl, substituted aryl, heteroaryl and substituted heteroaryl;

$R^8$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, alkylthio, substituted alkylthio, acyl and $(R^9)_3Si$; and each $R^9$ is independently selected from the group consisting of alkyl, substituted alkyl, alkoxy, substituted alkoxy, cycloalkyl, substituted cycloalkyl, aryl, substituted aryl, heteroaryl and substituted heteroaryl.

In one embodiment of formula III, X is O.

In another embodiment of formula III, $R^7$ is selected from the group consisting of deuterium, alkyl and substituted alkyl.

In yet another embodiment of formula III, $R^8$ is selected from the group consisting of hydrogen, alkyl, substituted alkyl, cycloalkyl, substituted cycloalkyl, aryl, substituted aryl, heteroaryl, substituted heteroaryl and $(R^9)_3Si$; and each $R^9$ is independently selected from the group consisting of alkyl, substituted alkyl, alkoxy, substituted alkoxy, cycloalkyl, substituted cycloalkyl, aryl, substituted aryl, heteroaryl and substituted heteroaryl.

In a certain embodiment of formula III, X is O; $R^7$ is alkyl; $R^8$ is selected hydrogen or $(R^9)_3Si$; and each $R^9$ is alkyl, in which each alkyl may either be the same or different.

In yet another aspect, the present invention discloses a method of performing a stereoselective reaction without use of a solvent comprising contacting a reactant with a chiral reagent under sonicating conditions to form an excess of an enantiomer, wherein the enantiomer is of formula IVa or IVb:

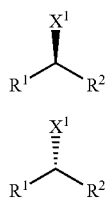

wherein:

$X^1$ is selected from the group consisting of OH, SH, and $NHR^3$;

$R^1$ and $R^2$ are independently selected from the group consisting of hydrogen, deuterium, halo, nitro, cyano, alkyl, substituted alkyl, alkenyl, substituted alkenyl, alkynyl, substituted alkynyl, haloalkyl, alkoxy, substituted alkoxy, cycloalkyl, substituted cycloalkyl, aryl, substituted aryl, heteroaryl, substituted heteroaryl, amino, substituted amino, aminoacyl, acylamino, alkylthio, substituted alkylthio, with the proviso that $R^1$ is not identical to $R^2$;

R³ is selected from the group consisting of hydrogen, alkyl, substituted alkyl, aryl, substituted aryl, —S(O)R⁴, —C(O)R⁴—NR⁵R⁵;

R⁴ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino; and each R⁵ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both R⁵ can be attached with an optional C(O) to form a heterocycle.

In one embodiment, the enantiomer is of the formula Va or Vb:

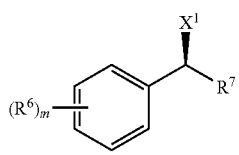

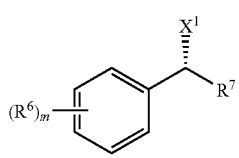

wherein:

$X^1$ is selected from the group consisting of OH, SH, and $NHR^3$;

$R^3$ is selected from the group consisting of hydrogen, alkyl, substituted alkyl, aryl, substituted aryl, —S(O)R⁴, —C(O)R⁴—NR⁵R⁵;

$R^4$ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino;

each $R^5$ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both $R^5$ can be attached with an optional C(O) to form a heterocycle;

each $R^6$ is independently selected from the group consisting of halo, nitro, cyano, hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino, aminoacyl, acylamino, alkylthio, substituted alkylthio, and acyl;

$R^7$ is selected from the group consisting of hydrogen, deuterium, alkyl, substituted alkyl, haloalkyl, cycloalkyl, substituted cycloalkyl, aryl, substituted aryl, heteroaryl and substituted heteroaryl; and m is an integer from 0 to 5.

In another embodiment, the enantiomer is of the formula VIa or VIb:

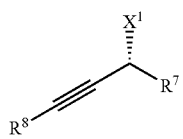

wherein:

$X^1$ is selected from the group consisting of OH, SH, and $NHR^3$;

$R^3$ is selected from the group consisting of hydrogen, alkyl, substituted alkyl, aryl, substituted aryl, —S(O)R⁴, —C(O)R⁴ and —NR⁵R⁵;

$R^4$ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino;

each $R^5$ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both $R^5$ can be attached with an optional C(O) to form a heterocycle;

$R^7$ is selected from the group consisting of hydrogen, deuterium, alkyl, substituted alkyl, haloalkyl, cycloalkyl, substituted cycloalkyl, aryl, substituted aryl, heteroaryl and substituted heteroaryl;

$R^8$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, alkylthio, substituted alkylthio, acyl and $(R^9)_3Si$; and each $R^9$ is independently selected from the group consisting of alkyl, substituted alkyl, alkoxy, substituted alkoxy, cycloalkyl, substituted cycloalkyl, aryl, substituted aryl, heteroaryl and substituted heteroaryl.

In one aspect, the present invention discloses a method of performing a stereoselective reaction without use of a solvent comprising contacting a reactant with a chiral reagent under sonication conditions to form an excess of an enantiomer, wherein the reaction is a reduction of an aldehyde, ketone, alpha-haloketone, aldimine, imine or alpha-haloimine; provided that the chiral reagent is not covalently bonded to the reactant; and further provided that the chiral reagent is not N-benzyl-1-hydroxy-N,N-dimethyl-1-phenylpropan-2-aminium bromide.

Also disclosed herein is a method of reducing an aryl-d-aldehyde without the use of a solvent comprising of sonicating the aryl-d-aldehyde in the presence of B-isopinocampheyl-9-borabicyclo[3.3.1]nonane to form an aryl-d-methanol. In one aspect, the aryl-d-aldehyde is selected from the group consisting of d-2,6-dimethylbenzaldehyde and d-2,4,6-trimethylbenzaldehyde.

Also disclosed herein is a method of reducing a ketone without the use of a solvent comprising of sonicating the ketone in the presence of B-isopinocampheyl-9-borabicyclo

[3.3.1]nonane to form an alcohol. In a certain aspect, the ketone is selected from the group consisting of acetophenone, tetradec-1-yn-3-one and 4-methyl-1-(trimethylsilyl)pent-1-yn-3-one.

The above described compounds would be the product of a number of organic reactions, such as reductions, alkylations, epoxidations, cyclizations, aldol additions, halogenations, Diels-Alder reactions, cycloadditions, Baylis-Hillman reactions and protonations. The reactions are more thoroughly discussed below.

2. Detailed Reactions

The methods described herein improve the stereoselectivity and/or yield of a number of chemical reactions performed under solvent-free conditions. For example, the method described herein substantially increases stereoselection in the Alpine Borane® reduction of 2,4,6-trimethyl-d-benzaldehyde under solvent-free conditions.

| Method | Time (hour) | Yield (%) | Enantiomeric excess (%) |
| --- | --- | --- | --- |
| Mechanical Stirring | 96 | trace | Not determined |
| Mechanical Stirring in refluxing THF | 2 | 87 | 88 |
| Sonication | 3 | 50 | 96 |

In addition, the method described herein substantially increases stereoselection in the Alpine Borane® reduction of 2,6-dimethyl-d-benzaldehyde under solvent-free conditions.

| Method | Time (hour) | Yield (%) | Enantiomeric excess (%) |
| --- | --- | --- | --- |
| Mechanical Stirring in refluxing THF | 2 | 80 | 75 |
| Sonication | 3 | 50 | 96 |

The method described herein allows for a decrease in reaction time for the stereoselective reduction of α,β-acetylenic ketones with Alpine Borane® under solvent-free conditions.

| Method | Time (hour) | Yield (%) | Enantiomeric excess (%) |
| --- | --- | --- | --- |
| Mechanical Stirring | 4 | 60 | 97 |
| Sonication | 1 | 61 | 99 |

| Method | Time (hour) | Yield (%) | Enantiomeric excess (%) |
| --- | --- | --- | --- |
| Mechanical Stirring | 48 | 95 | 74 |
| Sonication | 14 | 88 | 96 |

Other benefits may be observed by using the methods of the invention such as decreased reaction time. Ketones are notoriously difficult substrates for the stereoselective reduction using the Alpine Borane®. In the following example, sonication does not further increase the enantiomeric excess in the stereoselective reduction of acetophenone. However, the yield increased during a decreased reaction time when compared to mechanical stirring.

| Method | Time (hour) | Yield (%) | Enantiomeric excess (%) |
| --- | --- | --- | --- |
| Mechanical Stirring | 4 | 10 | 94 |
| Sonication | 1 | 33 | 93 |

In certain embodiments, the present invention discloses a method of performing a stereoselective reaction with a diminished amount solvent comprising sonicating a reactant in the presence of a chiral reagent to form a product; provided that the chiral reagent is not covalently bonded to the reactant; and further provided that the chiral reagent is not N-benzyl-1-hydroxy-N,N-dimethyl-1-phenylpropan-2-aminium bromide. The term "diminished amount of solvent" is intended to refer to an amount less than typically used in the same reaction. For example, the methods disclosed herein can be conducted at a higher concentration than previously used for the same reaction.

The method described herein allows for a decrease in reaction time with an increased yield for the stereoselective cyclization shown below utilizing L-proline in DMF for the sonication reaction at 20-30° C. versus conventional mechanical stirring at room temperature.

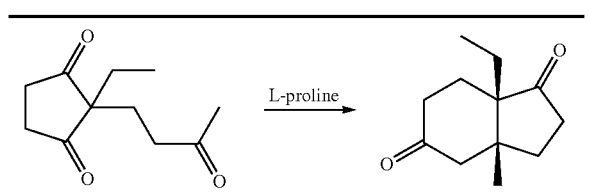

| Method | Time (hour) | Yield (%) | Enantiomeric excess (%) |
|---|---|---|---|
| Mechanical Stirring in DMF | 21.5 | 52 | 93 |
| Sonication in DMF | 4 | 62 | 93 |

The data presented above illustrates that the enantiomeric excess of the reduction reaction is either improved or does not change, whereas the reaction time is noticeably shorter. The above sonication reactions illustrate an improvement over the corresponding using mechanical stirring. It is contemplated that the methods described herein are useful for a number of other reductions.

Additional reactions may also benefit from the methods of the invention. It is contemplated that the following reactions would benefit from sonicating under solvent-free conditions.

One such example is the Baylis-Hillman reaction. The Baylis-Hillman reaction is the condensation between the α-position of an activated double bond with an electrophile such as an aldehyde. Aldehydes are the most commonly used electrophile in the Baylis-Hillman reaction. However, aromatic aldehydes are extremely slow to react (typically 1-4 weeks). Chiral catalysts include chiral amines and phosphines. Also chiral Lewis acids in the presence of an achiral amine or phosphine catalyst is also included (McDougal et al. (2003) *J. Am. Chem. Soc.* 125: 12094-12095).

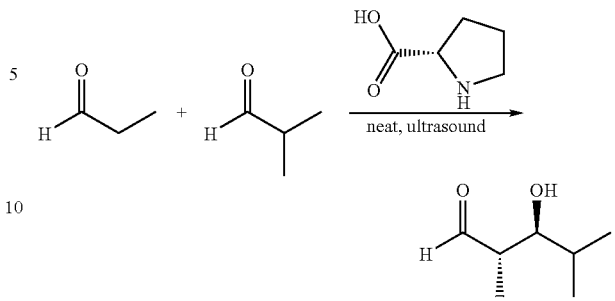

Another example of a reaction that is improve if performed under the reaction conditions of the disclosed invention is the Diels-Alder reaction. The Diels-Alder reaction is a [4+2]-cycloaddition of a conjugated diene and a dienophile (an alkene or alkyne), more specifically, an electrocyclic reaction that involves the 4 π-electrons of the diene and 2 π-electrons of the dienophile. The driving force of the reaction is the formation of new σ-bonds, which are energetically more stable than the π-bonds. With its broad scope and simplicity of operation, the Diels-Alder is the most powerful synthetic method for unsaturated six-membered rings. A variant is the hetero-Diels-Alder, in which either the diene or the dienophile contains a heteroatom, most often nitrogen or oxygen. This alternative constitutes a powerful synthesis of six-membered ring heterocycles. Although both simple and powerful, these reactions are very slow and can take up to three days for completion. A number of chiral catalysts could be employed in the method disclosed herein, such as chiral oxazaborolidine-aluminum bromide complexes (Liu, et al. (2007) *J. Am. Chem. Soc.* 129: 1498-1499) and chiral titanium (IV) Schiff-base complexes which have been shown to be useful for the hetero-Diels-Alder reaction (Fan, et al. (2005) *Eur. J. Org. Chem.* 3542-3552).

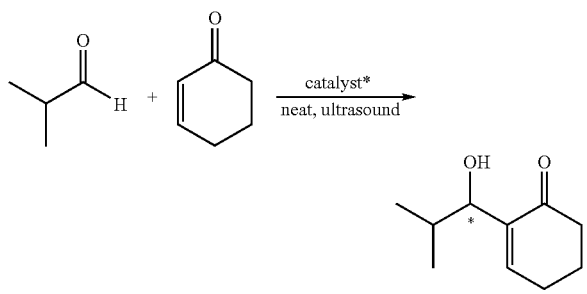

Another reaction that might improve if performed under the reaction conditions of the disclosed invention is the aldol addition reaction. The aldol addition reaction occurs when the enolate of an aldehyde or a ketone reacts at the α-carbon with the carbonyl of another molecule under basic or acidic conditions to obtain β-hydroxy aldehyde or ketone. These reactions are typically very slow and can take up to two days to form product even at room temperature. Various chiral catalysts could be employed in the method disclosed herein, such as organocatalysts like proline (Northrup, et al. (2002) *J. Am. Chem. Soc.* 124: 6798-6799) as well as organometallic catalysts like organozinc catalysts (Trost, et al. (2001) *Org. Lett.* 3: 2497-2500).

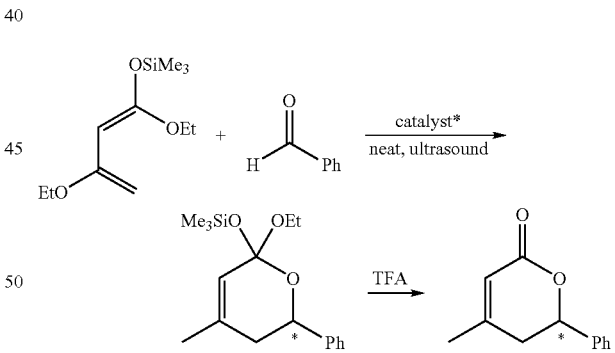

Additionally, it is contemplated that alkylation reactions are improved if performed under the reaction conditions described herein. Alkylation reactions, especially when performed asymmetrically, are one of the most useful methods for enantioselective carbon-carbon bond formation. The alkyl group may be transferred as an alkyl carbocation, a free radical, a carbanion or a carbene (or their equivalents). Various alkylating reagents that can be modified with either a chiral ligand or contain chirality on the alkylating group are known and include organometallic compounds such as Grignard (organomagnesium), organolithium, organocopper, organozinc and organoindium reagents as well as other metal-catalyzed methods such as palladium, rhodium, nickel and the like. Such compounds typically can add to an electron-deficient carbon atom such as a carbonyl group.

It is also contemplated that asymmetric epoxidation reactions are facilitated if performed under the reaction conditions disclosed herein. Examples of such highly enantioselective alkene epoxidations can be found in the Sharpless epoxidation (Katsuki, et al. (1980) *J. Am. Chem. Soc.* 102: 5974), the Jacobsen epoxidation (Zhang, et al. (1990) *J. Am. Chem. Soc.* 112, 2801-2803) and the Shi epoxidation (Wang, et al. (1997) *J. Am. Chem. Soc.* 119:46 11224-11235) methods.

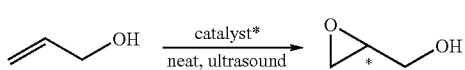

In addition to the reactions described above, it is thought that other asymmetric reactions are also enhanced under the reaction conditions disclosed herein. The enantioselective synthesis of complex molecules typically requires mild reaction conditions, as each subsequent step has the possibility of destroying the work of a prior reagent. Such is the case with a stereocenter alpha to a carbonyl, as the proton is inherently labile and thus prone to racemization in either acidic or basic media. Accordingly, the asymmetric protonation reaction, such as the enantioselective protonation of a silyl enol ether using a cinchona alkaloid catalyst, have been developed to circumvent this problem. However, even at room temperature, 12 hours is required (Poisson, et al. (2007) *Angew. Chem. Int. Ed.* 46:37 7090-7093).

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description.

Example 1

General Experimental for Performing a Stereoselective Reaction Under Solvent-Free Conditions Flame dry a reaction flask and cool under argon. Charge the reaction flask with reagents and chiral catalyst(s) if required. Expose reaction flask to ultrasound. Reactions can be monitored for completion using a variety of methods including both manual and/or automated thin layer chromatography (TLC), gas chromatography (GC), high performance liquid chromatography (HPLC), mass spectrometry (MS), mass spectrometry in tandem with liquid chromatography (LC-MS) or gas chromatography (GC-MS), Infrared (IR), nuclear magnetic resonance (NMR), or any other method commonly known in the art. Once the reaction the desired yield, remove reaction flask and work-up as usual.

Example 2

Alpine Borane® Reduction

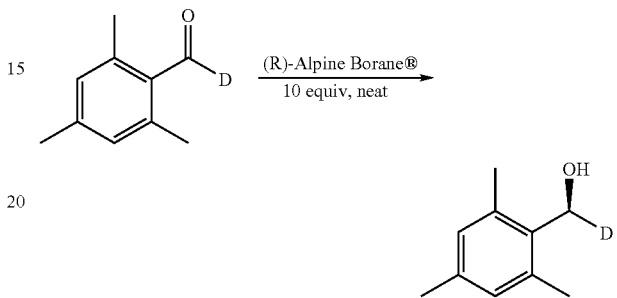

An oven dried round bottom flask was cooled under argon and charged with (R)-Alpine Borane® (10 equiv.). The flask was sealed and reducing 2,4,6-trimethyl-d-benzaldehyde (1 equiv) was added via syringe. The flask was lowered into the sonication bath and allowed to react for c.a. 3 hours. The flask was then removed from the sonication bath, diluted with a suitable solvent, transferred to separatory funnel and extracted.

The following substrates were reduced under similar reaction conditions to those described herein above.

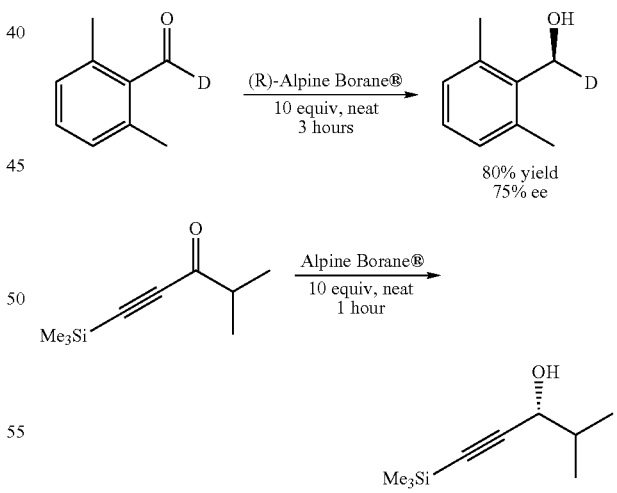

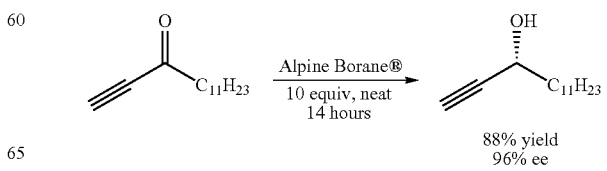

-continued

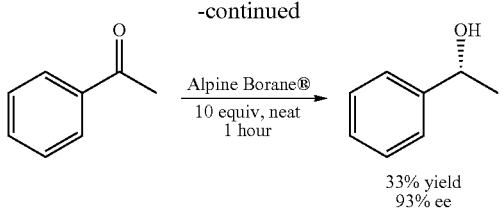

33% yield
93% ee

Example 3

Cyclization

The stereoselective cyclization of 2-ethyl-2-(3-oxobutyl)cyclopentane-1,3-dione was performed in DMF under the reaction conditions disclosed above.

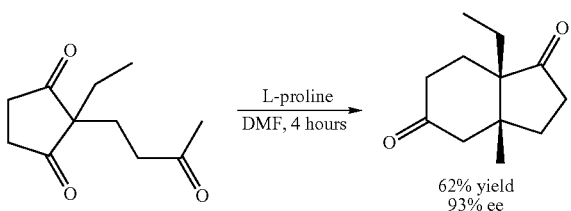

62% yield
93% ee

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES i) Lindley, J.; Mason, T. J. "Sonochemistry: Part 2—Synthetic Applications" Chem. Soc. Rev. 1987, 16, 275-311 and references therein.
ii) Tuncay, A.; Dustman, J. A.; Fisher, G.; Tuncay, C. I. "Ultrasound Promoted Hypervalent Iodine Reactions: α-Tosyloxylation of Ketones with [Hydroxy(Toxyloxy)Iodo]Benzene" Tetrahedron Lett. 1992, 33, 7647-7650.
iii) Mirza-Aghayan, M.; Etemad-Moghadam, Guita; Zaparucha, A.; Berlan, J.; Loupy, A.; Koenig, M. "Ultrasound Irradiation Effects on the Asymmetric Michael Reaction" Tetrahedron: Asymmetry 1995, 11, 2643-2646.
iv) Suslick, K. S.; Schubert, P. F.; Goodale, J. W. "Sonochemistry and Sonocatalysis of Iron Carbonyls" J. Am. Chem. Soc. 1981, 103, 7342-7344.
v) Suslick; Goodale, J. W.; Schubert, P. F.; Wang, H. H. "Sonochemistry and Sonocatalysis of Metal Carbonyls" J. Am. Chem. Soc. 1983, 105, 5781.
vi) Brown, H. C.; Racherla, U. S. "Ultrasonics in Organoborane Chemistry, A Novel and Powerful Method for Rapid Hydroboration" Tetrahedron Lett. 1985, 26, 2187-2190.
vii) Hickenboth, C. R.; Moore, J. S.; White, S. R.; Sottos, N. R.; Baudry, J.; Wilson, S. R. "Biasing Reaction Pathways with Mechanical Force" Nature 2007, 446, 423-427.
viii) Suslick, K. S. "Sonochemistry" Science 1990, 247, 1439-1445.
ix) Suslick, K. S.; Cline, R. E., Jr.; Hammerton, D. A. "The Sonochemical Hot Spot" J. Am. Chem. Soc. 1986, 108, 5641-5642.
x) Fujikawa, S.; Akamatsu, T. "Effects of the Non-equilibrium Condensation of Vapor on the Pressure Wave Produced by the Collapse of a Bubble in a Liquid" J. Fluid Mech. 1980, 97, 481-512.
xi) Flannigan, D. J.; Hopkins, S. D.; Camara, C. G.; Putterman, S. J.; Suslick, K. S. "Measurement of Pressure and Density Inside a Single Sonoluminescing Bubble" Phys. Rev. Lett. 2006, 96, 204301-1-204301-4.
xii) Asano, T.; Le Noble, W. J. "Activation and Reaction Volumes in Solution" Chem. Rev. 1978, 78, 407-489.
xiii) Matsumoto, K. "Organic Synthesis under High Pressure II" Synthesis 1985, 999-1027.
xv) Jenner, G. "High Pressure and Selectivity in Organic Reactions" Tetraheron 1997, 53, 2669-2695.
xvi) Jenner, G. "Comparative Activation Modes in Organic Synthesis. The Specific Role of High Pressure." Tetrahedron 2002, 58, 5185-5202.
xvii) Cherest, M.; Felkin, H.; Prudent, N. "Torsional Strain Involving Partial Bonds. The Stereochemistry of the Lithium Aluminum Hydride Reduction of Some Simple Open-Chain Ketones" Tetrahedron Lett. 1968, 9, 2199-2204.
xviii) West, J. D.; Stafford, S. E.; Meyer, M. P. "A Mechanistic Probe for Asymmetric Reactions: Deuterium Isotope Effects at Enantiotopic Groups" J. Am. Chem. Soc. 2008, 130, 7816-7817.
xix) Tietze, L. F.; Hübsch, T.; Voss, E.; Buback, M.; Tost, W. "Intermolecular Hetero-Diels-Alder Reactions of Enamino Ketones at High Pressure. The First Significant Pressure-induced Diastereoselectivity in Organic Transformations" J. Am. Chem. Soc. 1988, 110, 4065-4066.
xx) Yamamoto, Y.; Maruyama, K.; Matsumoto, K. "Organometallic High-Pressure Reactions. 2. Aldol Reaction of Silyl Enol Ethers Under Neutral Conditions" J. Am. Chem. Soc. 1983, 105, 6963-6965.

What is claimed is:

1. A method of performing a stereoselective reaction without use of a solvent comprising contacting a reactant with a chiral reagent under sonication conditions to form an excess of an enantiomer; provided that the chiral reagent is not covalently bonded to the reactant; and further provided that the chiral reagent is not N-benzyl-1-hydroxy-N,N-dimethyl-1-phenylpropan-2-aminium bromide.
2. The method of claim 1, wherein the stereoselective reaction is one or more of reductions, alkylations, cyclizations, epoxidations, aldol additions, halogenations, Diels-Alder reactions, cycloaddition reactions, Baylis-Hillman reactions or protonations.
3. The method of claim 1, wherein the stereoselective reaction is a reduction.
4. The method of claim 3, wherein the reduction is a reduction of an aldehyde.
5. The method of claim 1, wherein the a chiral reagent is B-isopinocampheyl-9-borabicyclo[3.31]nonane.
6. The method of claim 1, wherein the sonication conditions comprise sonicating at a power of from about 24 Watts to about 240 Watts.
7. The method of claim 6, wherein the power is about 80 Watts.
8. The method of claim 1, wherein the sonication conditions comprise sonicating at a frequency of from about 40 kHz to about 270 kHz.
9. The method of claim 8, wherein the frequency is about 40 kHz.
10. The method of claim 1, wherein the sonication conditions comprise sonicating at a temperature of from about −78° C. to about 65° C.

11. The method of claim 10, wherein the temperature is from about 20° C. to about 40° C.

12. The method of claim 1, wherein the enantiomer is present in an enantiomeric excess greater than an enantiomeric excess in a corresponding stereoselective reaction that does not employ sonication conditions and is performed without use of a solvent comprising contacting the reactant with the chiral reagent to form an excess of the enantiomer.

13. The method of claim 1, wherein the enantiomer is produced in a yield greater than a yield of the enantiomer in a corresponding stereoselective reaction that does not employ sonication conditions and is performed without use of a solvent comprising contacting the reactant with the chiral reagent to form an excess of the enantiomer.

14. A method of performing a stereoselective reaction without use of a solvent comprising contacting a reactant with a chiral reagent under sonicating conditions to form an excess of an enantiomer, wherein the reactant is of formula I;

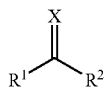
I wherein:
X is selected from the group consisting of O, S, and NR³;
R¹ and R² are independently selected from the group consisting of hydrogen, deuterium, halo, nitro, cyano, alkyl, substituted alkyl, alkenyl, substituted alkenyl, alkynyl, substituted alkynyl, haloalkyl, alkoxy, substituted alkoxy, cycloalkyl, substituted cycloalkyl, aryl, substituted aryl, heteroaryl, substituted heteroaryl, amino, substituted amino, aminoacyl, acylamino, alkylthio, and substituted alkylthio, with the proviso that R¹ is not identical to R²;
R³ is selected from the group consisting of hydrogen, alkyl, substituted alkyl, aryl, substituted aryl, —S(O)R⁴, —C(O)R⁴, and —NR⁵R⁵;
R⁴ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, and substituted amino; and
each R⁵ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both R⁵ can be attached with an optional C(O) to form a heterocycle;
provided that the chiral reagent is not covalently bonded to the reactant; and
further provided that the chiral reagent is not N-benzyl-1-hydroxy-N,N-dimethyl-1-phenylpropan-2-aminium bromide.

15. The method of claim 14, wherein X is O.

16. The method of claim 14, wherein R¹ and R² are independently selected from the group consisting of hydrogen, deuterium, alkyl, substituted alkyl, alkenyl, substituted alkenyl, alkynyl, substituted alkynyl, haloalkyl, cycloalkyl, substituted cycloalkyl, aryl, substituted aryl, heteroaryl, and substituted heteroaryl.

17. The method of claim 16, wherein R¹ and R² are independently selected from the group consisting of deuterium, alkyl, substituted alkyl, alkynyl, substituted alkynyl, haloalkyl, aryl, and substituted aryl.

18. The method of claim 16, wherein the a chiral reagent is B-isopinocampheyl-9-borabicyclo[3.3.1]nonane.

19. The method of claim 14, wherein the enantiomer is of the formula IVa or IVb:

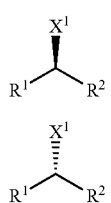

wherein:
X¹ is selected from the group consisting of OH, SH, and NHR³;
R³ is selected from the group consisting of hydrogen, alkyl, substituted alkyl, aryl, substituted aryl, —S(O)R⁴, —C(O)R⁴—NR⁵R⁵;
R⁴ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino; and
each R⁵ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both R⁵ can be attached with an optional C(O) to form a heterocycle.

20. The method of claim 14, wherein the reactant has the following formula:

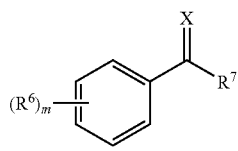
II wherein:
X is selected from the group consisting of O, S, and NR³;
R³ is selected from the group consisting of hydrogen, alkyl, substituted alkyl, aryl, substituted aryl, —S(O)R⁴, —C(O)R⁴—NR⁵R⁵;
R⁴ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino;
each R⁵ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both R⁵ can be attached with an optional C(O) to form a heterocycle;
each R⁶ is independently selected from the group consisting of halo, nitro, cyano, hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino, aminoacyl, acylamino, alkylthio, substituted alkylthio, and acyl;

R$^7$ is selected from the group consisting of hydrogen, deuterium, alkyl, substituted alkyl, haloalkyl, cycloalkyl, substituted cycloalkyl, aryl, substituted aryl, heteroaryl and substituted heteroaryl; and m is an integer from 0 to 5.

21. The method of claim 20, wherein X is O.

22. The method of claim 20, wherein each R$^6$ is independently selected from the group consisting of alkyl and substituted alkyl; and m is an integer from 0 to 3.

23. The method of claim 20, wherein R$^7$ is selected from the group consisting of deuterium, alkyl and substituted alkyl.

24. The method of claim 20, wherein the a chiral reagent is B-isopinocampheyl-9-borabicyclo[3.3.1]nonane.

25. The method of claim 20, wherein X is O; each R$^6$ is independently selected from the group consisting of alkyl and substituted alkyl; m is an integer from 0 to 3; and R$^7$ is selected from the group consisting of deuterium and alkyl.

26. The method of claim 20, wherein the enantiomer is of the formula Va or Vb:

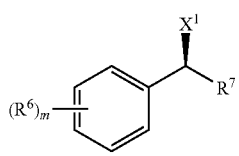

Va

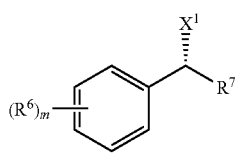

Vb wherein:

X$^1$ is selected from the group consisting of OH, SH, and NHR$^3$;

R$^3$ is selected from the group consisting of hydrogen, alkyl, substituted alkyl, aryl, substituted aryl, —S(O)R$^4$, —C(O)R$^4$ —NR$^5$R$^5$;

R$^4$ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino;

each R$^5$ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both R$^5$ can be attached with an optional C(O) to form a heterocycle.

27. The method of claim 14, wherein the reactant has the following formula:

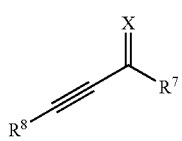

III wherein:

X is selected from the group consisting of O, S, and NR$^3$;

R$^3$ is selected from the group consisting of hydrogen, alkyl, substituted alkyl, aryl, substituted aryl, —S(O)R$^4$, —C(O)R$^4$ and —NR$^5$R$^5$;

R$^4$ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino;

each R$^5$ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both R$^5$ can be attached with an optional C(O) to form a heterocycle;

R$^7$ is selected from the group consisting of hydrogen, deuterium, alkyl, substituted alkyl, haloalkyl, cycloalkyl, substituted cycloalkyl, aryl, substituted aryl, heteroaryl and substituted heteroaryl;

R$^8$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, alkylthio, substituted alkylthio, acyl and (R$^9$)$_3$Si; and each R$^9$ is independently selected from the group consisting of alkyl, substituted alkyl, alkoxy, substituted alkoxy, cycloalkyl, substituted cycloalkyl, aryl, substituted aryl, heteroaryl and substituted heteroaryl.

28. The method of claim 27, wherein X is O.

29. The method of claim 27, wherein R$^7$ is selected from the group consisting of deuterium, alkyl and substituted alkyl.

30. The method of claim 27, wherein R$^8$ is selected from the group consisting of hydrogen, alkyl, substituted alkyl, cycloalkyl, substituted cycloalkyl, aryl, substituted aryl, heteroaryl, substituted heteroaryl and (R$^9$)$_3$Si; and each R$^9$ is independently selected from the group consisting of alkyl, substituted alkyl, alkoxy, substituted alkoxy, cycloalkyl, substituted cycloalkyl, aryl, substituted aryl, heteroaryl and substituted heteroaryl.

31. The method of claim 27, wherein the a chiral reagent is B-isopinocampheyl-9-borabicyclo[3.3.1]nonane.

32. The method of claim 27, wherein X is O; R$^7$ is alkyl; R$^8$ is selected hydrogen or (R$^9$)$_3$Si; and each R$^9$ is alkyl.

33. The method of claim 27, wherein the enantiomer is of the following formula:

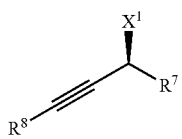

VIa

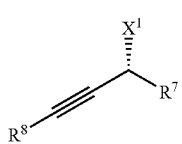

VIb wherein:

X$^1$ is selected from the group consisting of OH, SH, and NHR$^3$;

R$^3$ is selected from the group consisting of hydrogen, alkyl, substituted alkyl, aryl, substituted aryl, —S(O)R$^4$, —C(O)R$^4$ and —NR$^5$R$^5$;

R⁴ is selected from the group consisting of hydroxyl, alkyl, substituted alkyl, alkoxy, substituted alkoxy, cycloalkyl, substituted cycloalkyl, aryl, substituted aryl, heteroaryl, substituted heteroaryl, amino, substituted amino;

each R⁵ is independently selected from the group consisting of alkyl, substituted alkyl, alkoxy, substituted alkoxy, cycloalkyl, substituted cycloalkyl, aryl, substituted aryl, heteroaryl, substituted heteroaryl, aminoacyl, acylamino, alkylthio, substituted alkylthio, and acyl, or both R⁵ can be attached with an optional C(O) to form a heterocycle.

34. A method of performing a stereoselective reaction without use of a solvent comprising contacting a reactant with a chiral reagent under sonication conditions to form an excess of an enantiomer, wherein the reaction is a reduction of an aldehyde, ketone, alpha-haloketone, aldimine, imine or alpha-haloimine; provided that the chiral reagent is not covalently bonded to the reactant; and further provided that the chiral reagent is not N-benzyl-1-hydroxy-N,N-dimethyl-1-phenylpropan-2-aminium bromide.

35. A method of reducing an aryl-d-aldehyde without use of a solvent comprising contacting the aryl-d-aldehyde under sonication conditions with B-isopinocampheyl-9-borabicyclo[3.3.1]nonane to form an aryl-d-methanol.

36. The method of claim 35, wherein the aryl-d-aldehyde is selected from the group consisting of d-2,6-dimethylbenzaldehyde and d-2,4,6-trimethylbenzaldehyde.

37. A method of reducing a ketone without solvent comprising contacting the ketone with B-isopinocampheyl-9-borabicyclo[3.3.1]nonane under sonication conditions to form an alcohol.

38. The method of claim 37, wherein the ketone is selected from the group consisting of acetophenone, tetradec-1-yn-3-one and 4-methyl-1-(trimethylsilyl)pent-1-yn-3-one.

* * * * *